United States Patent
Sugimoto et al.

(10) Patent No.: US 9,463,065 B2
(45) Date of Patent: Oct. 11, 2016

(54) METHOD OF TREATING A LIVING BODY TISSUE

(71) Applicant: TERUMO KABUSHIKI KAISHA, Shibuya-ku, Tokyo (JP)

(72) Inventors: Ryota Sugimoto, Tokyo (JP); Yousuke Ootani, Tokyo (JP); Ichirou Hirahara, Kanagawa-ken (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 0 days.

(21) Appl. No.: 14/878,422

(22) Filed: Oct. 8, 2015

(65) Prior Publication Data

US 2016/0022359 A1   Jan. 28, 2016

Related U.S. Application Data

(63) Continuation of application No. 13/996,382, filed as application No. PCT/JP2011/078911 on Dec. 14, 2011.

(30) Foreign Application Priority Data

Dec. 21, 2010 (JP) ................. 2010-283913

(51) Int. Cl.
*A61B 18/14* (2006.01)
*A61B 18/00* (2006.01)

(52) U.S. Cl.
CPC .... *A61B 18/1492* (2013.01); *A61B 2018/0022* (2013.01); *A61B 2018/00285* (2013.01); *A61B 2018/00434* (2013.01); *A61B 2018/00577* (2013.01); *A61B 2018/00595* (2013.01)

(58) Field of Classification Search
CPC ...... A61B 18/04; A61B 18/08; A61B 18/10; A61B 18/12; A61B 18/1266; A61B 18/14; A61B 18/1442; A61B 18/1445; A61B 18/1448; A61B 18/1492; A61B 2018/0022; A61B 2018/00285; A61B 18/00577
USPC ............ 606/41–50; 607/1–3, 9, 72
See application file for complete search history.

(56) References Cited

U.S. PATENT DOCUMENTS 5,779,698 A * 7/1998 Clayman ............... A61B 17/22
                                                                 604/114
6,322,559 B1   11/2001 Daulton et al.
(Continued)

FOREIGN PATENT DOCUMENTS

JP   2003-510160 A   3/2003
JP   2003-260063 A   9/2003
(Continued)

OTHER PUBLICATIONS

International Search Report (PCT/ISA/210) issued on Jan. 17, 2012, by the Japanese Patent Office as the International Searching Authority for International Application No. PCT/JP2011/078911.
(Continued)

*Primary Examiner* — Michael Peffley
*Assistant Examiner* — Khadijeh Vahdat
(74) *Attorney, Agent, or Firm* — Buchanan Ingersoll & Rooney PC

(57) ABSTRACT

A method is disclosed for treating a living body tissue by cauterizing a sympathetic nerve around a renal artery to block a neurotransmission function of the sympathetic nerve. The method includes inserting a balloon catheter including a balloon on a distal end side of a shaft into a body cavity, and delivering the balloon to the renal artery; inflating the balloon that has been delivered to the renal artery; puncturing a blood vessel wall with at least one protrusive member disposed on an outer surface of the balloon when the balloon is inflated; and after puncturing the blood vessel wall with the protrusive member, cauterizing the sympathetic nerve within a region at a periphery of an electrode disposed on a projecting tip end portion of the protrusive member by supplying a current to the electrode.

9 Claims, 9 Drawing Sheets

(56) References Cited

U.S. PATENT DOCUMENTS

| | | |
|---|---|---|
| 6,405,732 B1 | 6/2002 | Edwards et al. |
| 7,753,907 B2 | 7/2010 | DiMatteo et al. |
| 2003/0074039 A1 | 4/2003 | Puskas |
| 2003/0144658 A1 | 7/2003 | Schwartz et al. |
| 2003/0153905 A1* | 8/2003 | Edwards ............ A61B 18/1492 606/41 |
| 2003/0229370 A1 | 12/2003 | Miller |
| 2005/0070888 A1 | 3/2005 | Dimatteo et al. |
| 2005/0288730 A1 | 12/2005 | Deem et al. |
| 2007/0129720 A1 | 6/2007 | Demarais et al. |
| 2007/0203549 A1* | 8/2007 | Demarais ................. A61N 1/05 607/72 |
| 2007/0265617 A1 | 11/2007 | Falkenstein et al. |
| 2009/0306644 A1 | 12/2009 | Mayse et al. |
| 2013/0090637 A1* | 4/2013 | Sliwa ..................... A61B 18/24 606/14 |

FOREIGN PATENT DOCUMENTS

| | | |
|---|---|---|
| JP | 2005-529652 A | 10/2005 |
| JP | 2008-515544 A | 5/2008 |
| JP | 2010-509032 A | 3/2010 |
| WO | 97/32532 A1 | 9/1997 |
| WO | 2006/050134 A1 | 5/2006 |
| WO | 2007/078997 A2 | 7/2007 |
| WO | WO 2009/137819 A1 | 11/2009 |
| WO | 2011/056684 A2 | 5/2011 |
| WO | 2011/060200 A1 | 5/2011 |
| WO | 2011/130534 A2 | 10/2011 |

OTHER PUBLICATIONS

Written Opinion (PCT/ISA/237) issued on Jan. 17, 2012, by the Japanese Patent Office as the International Searching Authority for International Application No. PCT/JP2011/078911.

Extended European Search Report issued Jul. 28, 2016 by the European Patent Office in corresponding European Patent Application No. 11851737 (10 pages).

* cited by examiner

METHOD OF TREATING A LIVING BODY TISSUE

CROSS-REFERENCES TO RELATED APPLICATIONS

This application is a continuation of U.S. application Ser. No. 13/996,382, filed on Jun. 20, 2013, which claims priority to International Application No. PCT/JP2011/078911 filed on Dec. 14, 2011, designating the U.S., and which claims priority to Japanese Application No. 2010-283913 filed on Dec. 21, 2010, the entire content of each of which is incorporated herein by reference.

TECHNICAL FIELD

The present invention relates to a balloon catheter for being inserted into a body cavity and treating a desired living tissue therein, and an energizing (electrification) system incorporating such a balloon catheter.

BACKGROUND ART

There has been a finding that patients with intractable hypertension who find it difficult to improve their high blood pressure even by taking antihypertensive can expect their blood pressure to be lowered by severing or disrupting the sympathetic nerve around the renal artery to block neurotransmission.

It has been proposed in the art to percutaneously sever the sympathetic nerve around the renal artery using an ablation catheter. For example, Japanese Laid-Open Patent Publication No. 2008-515544 (PCT) discloses an ablation catheter for severing the sympathetic nerve around the renal artery, the ablation catheter including a helical electrode disposed around an inflatable balloon for contacting and energizing the inner wall of a blood vessel. Similarly, Japanese Laid-Open Patent Publication No. 2010-509032 (PCT) discloses an electrode disposed around a positioning member such as a balloon or the like, the electrode being expandable into contact with the inner wall of a blood vessel for energizing.

SUMMARY OF INVENTION

Normally, the sympathetic nerve around the renal artery is disposed in the vicinity of the adventitia. The above ablation catheter according to the background art has its electrode held in abutment with the inner surface of the renal artery and cauterizes the inner surface of the renal artery. Therefore, the ablation catheter tends to cauterize not only the sympathetic nerve in the vicinity of the adventitia, but also the entire blood vessel wall including the intima of the renal artery. In other words, since energy is transmitted to other regions than the target issue to be cauterized, i.e., the sympathetic nerve in the vicinity of the adventitia, the ablation catheter is likely to cause possible problems such as intimal thickening, thrombosis, etc.

The present invention has been made in view of the above drawbacks of the background art. It is an object of the present invention to provide a balloon catheter which is capable of selectively transmitting energy to a desired living tissue and an energizing system incorporating such a balloon catheter.

According to the present invention, there is provided a balloon catheter including a balloon on a distal end side of a shaft, comprising a protrusive member disposed on an outer surface of the balloon and extending outwardly from the outer surface of the balloon at least when the balloon is inflated, and an electrode disposed on a projecting tip end portion of the protrusive member, for transmitting energy to a living body tissue.

According to the present invention, there is also provided an energizing system comprising a balloon catheter including a balloon on a distal end side of a shaft and an electrode disposed on an outer surface of the balloon, for transmitting energy to a living body tissue, and a power supply for supplying a high-frequency current to the electrode, wherein the balloon catheter has a protrusive member disposed on the outer surface of the balloon and extending outwardly from the outer surface of the balloon at least when the balloon is inflated, and the electrode is disposed on a projecting tip end portion of the protrusive member.

With the above arrangement, the protrusive member which projects outwardly at least when the balloon is inflated is disposed on the outer surface of the balloon, and the electrode for transmitting energy to a living body tissue is disposed on a projecting tip end portion of the protrusive member. The electrode can be reliably delivered to a desired living body tissue which is present deeply in a blood vessel wall, for selectively transmitting energy to the living body tissue and its neighboring region. When the balloon is inflated in a renal artery, for example, the protrusive member cuts into or pushes a wall surface of the renal artery and delivers the electrode on the tip end portion of the protrusive member to a position in the vicinity of the adventitia of the renal artery for energizing. Consequently, the electrode can selectively cauterize a sympathetic nerve that is present around the adventitia of the renal artery while effectively preventing the overall blood vessel wall from being adversely affected by the energization.

If the protrusive member is insulative, then energy transmission from the protrusive member to the living body tissue is reliably blocked for smoother selective energy transmission to the desired living body tissue.

The protrusive member may serve as a cutting edge having the electrode on a leading end thereof for cutting into a blood vessel wall to deliver the electrode into the blood vessel wall. Alternatively, the protrusive member may serve as a pushing member having the electrode on a leading end thereof and having an abutment portion with an inner surface of a blood vessel for pushing the inner surface of the blood vessel wall toward an outer surface of the blood vessel wall, thereby deforming the blood vessel wall, to deliver the electrode to a desired position when the protrusive member is pressed against the inner surface of the blood vessel wall.

If the protrusive member is provided as at least a pair of protrusive members, and the electrodes disposed on the pair of protrusive members serve as a set of bipolar electrodes, then the living body tissue to be energized can be energized more locally, so that energy transmission to other living body tissues is prevented more reliably. The protrusive members may be provided in a plurality of arrays disposed along an axial direction of the balloon and at different circumferential phases of the balloon in the arrays. With this arrangement, the protrusive members are prevented from being concentrating circumferentially at a certain position along the direction in which the renal artery extends, and hence from cauterizing the blood vessel wall in an annular pattern at one location. In other words, the electrodes cauterizes the blood vessel wall at axially distributed positions, but prevents the blood vessel wall from being injured intensively at one location along the direction in which the blood vessel extends. Therefore, a sympathetic nerve that extends along the blood vessel is reliably cauterized by the electrodes that are disposed in axially distributed arrays, while at the same time any injury caused to the cauterized blood vessel is distributed to prevent the blood vessel from being greatly injured locally. The protrusive member may be disposed helically on the outer surface of the balloon.

If the protrusive member is shaped as a thin plate or a needle, then the protrusive member makes it possible to deliver the electrode on the tip end more smoothly deeply into the blood vessel wall.

The energy may comprise high-frequency energy. The living body tissue may comprise a nerve around a renal artery.

According to the present invention, the protrusive member which projects outwardly at least when the balloon is inflated is disposed on the outer surface of the balloon, and the electrode for transmitting energy to a living body tissue is disposed on a projecting tip end portion of the protrusive member. The electrode can be reliably delivered to a desired living body tissue which is present deeply in a blood vessel wall, for selectively transmitting energy only to the living body tissue and its neighboring region.

A method is disclosed for treating a living body tissue by cauterizing a sympathetic nerve around a renal artery to block a neurotransmission function of the sympathetic nerve, comprising the steps of: inserting a balloon catheter including a balloon on a distal end side of a shaft into a body cavity, and delivering the balloon to the renal artery; inflating the balloon that has been delivered to the renal artery; puncturing a blood vessel wall with at least one protrusive member disposed on an outer surface of the balloon when the balloon is inflated; and after puncturing the blood vessel wall with the protrusive member, cauterizing the sympathetic nerve within a region at a periphery of an electrode disposed on a projecting tip end portion of the protrusive member by supplying a current to the electrode.

DESCRIPTION OF EMBODIMENTS

Balloon catheters according to preferred embodiments of the present invention in relation to an energizing system which incorporates the balloon catheters will be described below with reference to the accompanying drawings.

Figure 1:
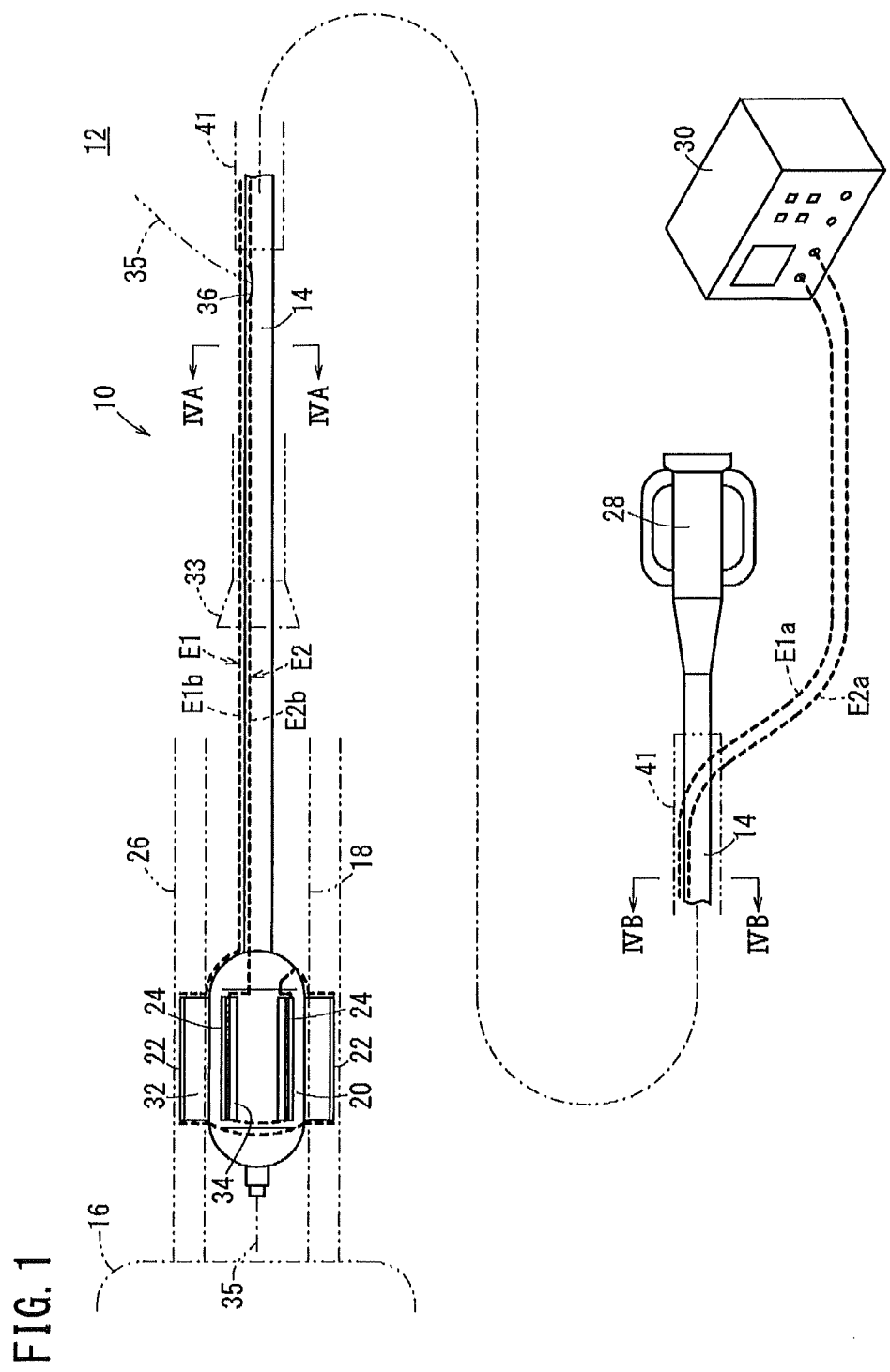
FIG. 1 is a view showing an energizing system in its entirety which incorporates a balloon catheter according to an embodiment of the present invention.
Figure 2:
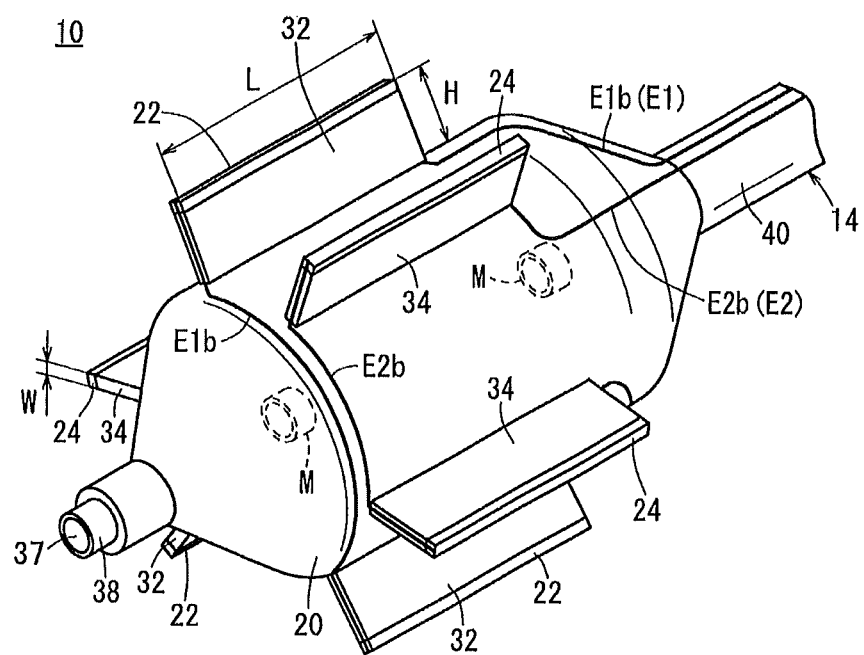
FIG. 2 is an enlarged perspective view of a distal end side of the balloon catheter shown in FIG. 1.

FIG. 1 is a view showing an energizing system 12 in its entirety which incorporates a balloon catheter 10 according to an embodiment of the present invention, and FIG. 2 is an enlarged perspective view of a distal end side of the balloon catheter 10 shown in FIG. 1.

The energizing system 12 is a medical instrument for treating a hypertension by blocking or disabling the neurotransmission function of a sympathetic nerve 26. In the treatment of the hypertension, the balloon catheter 10 has an elongate shaft 14 inserted into a body cavity, e.g., a renal artery 18 leading to a kidney 16, and a balloon 20 on a distal end side thereof which has a pair of electrodes 22, 24 on its surface. The electrodes 22, 24 are delivered into the blood vessel wall and energized to transmit energy to a region around the adventitia of the renal artery 18 for thereby cauterizing the sympathetic nerve 26. In FIGS. 1 and 2, a right side of the shaft 14 which is near a hub 28 will be referred to as a "proximal end (rear end, near region)" side, and a left side of the shaft 14 which is near the balloon 20 as a "distal end (far region)" side.

As shown in FIGS. 1 and 2, the energizing system 12 includes the balloon catheter (cutting catheter, ablation catheter) 10, and a high-frequency power supply (power supply) 30 for supplying a high-frequency current to a plurality of pairs of electrodes 22, 24 mounted on the balloon 20 of the balloon catheter 10. The high-frequency power supply 30 may have specifications properly selected depending on, e.g., a target to be treated by the balloon catheter 10. The high-frequency power supply 30 and the electrodes 22, 24 are interconnected by energizing paths E1, E2 (indicated by the broken lines in FIG. 1) extending in and along the shaft 14.

The balloon catheter 10 includes the shaft 14 which is slender and elongate, the balloon 20 disposed on the distal end side of the shaft 14, a plurality of protrusive members (protrusive pieces, cutting members, cutting edges, pushing members) 32, 34 which protrude radially-outwardly from an outer surface of the balloon 20, the electrodes 22, 24 mounted on respective projecting tip end portions of the protrusive members 32, 34 for transmitting energy to a living tissue, and the hub 28 disposed on the proximal end side of the shaft 14.

In FIG. 1, the balloon catheter 10 illustrated as a so-called rapid-exchange-type structure wherein the shaft 14 has an opening 36 formed in an intermediate portion thereof that is slightly closer to the distal end side, with a guide wire 35 extending out of the opening 36. However, the balloon catheter 10 may be of an over-the-wire-type structure wherein the guide wire 35 extends out of the hub 28 on the proximal end.

The balloon catheter 10 according to the present embodiment is of constitution similar to general balloon catheters for use in PTCA (Percutaneous Transluminal Coronary Angioplasty) except that the protrusive members 32, 34 and the electrodes 22, 24 are disposed on the outer surface of the balloon 20 and the energizing paths E1, E2 are provided which interconnect the high-frequency power supply 30 and the electrodes 22, 24. The constitutive details of the balloon catheter 10 which are similar to those of the general balloon catheters will not be described in detail below. For example, the shaft 14 of the balloon catheter 10 is of a dual-tube structure from the balloon 20 to the opening 36, which has an inner tube 38 which has a guide wire lumen 37 (see FIG. 4A) through which the guide wire 35 is inserted, and an outer tube 40 with an inflating lumen 39 formed between itself and the inner tube 38 for passage therein of an inflating fluid (e.g., a contrast medium) to be supplied to the balloon 20, and a single-tube structure from the opening 36 to the hub 28 (see FIG. 4B), which has the inflating lumen 39 in the outer tube 40 (or a proximal shaft, not shown). The balloon 20 of the balloon catheter 10 can be inflated when the inflating fluid is delivered thereto under pressure from a pressure applying device (not shown) such as an indeflator or the like via a luer taper mounted on the hub 28.

Each of the inner tube 38 and the outer tube 40 of the shaft 14 is in the form of a tube made of a polymeric material such as polyolefin, polyvinyl chloride, polyamide, polyamide elastomer, polyurethane, polyurethane elastomer, polyimide, fluororesin, or the like, or a mixture of these polymeric materials, or a multilayer tube of two or more of the above polymeric materials. The balloon 20 is made of essentially the same material or materials as the inner tube 38 and the outer tube 40.

Figure 3A:
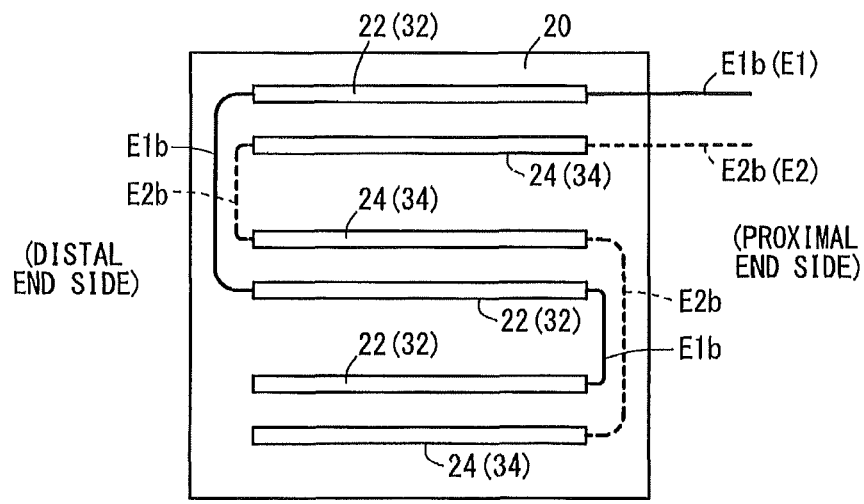
FIG. 3A is a view showing a cylindrical portion of the balloon of the balloon catheter as it is spread out 360° in the circumferential direction thereof.

FIG. 3A is a view showing a cylindrical portion of the balloon 20, i.e., a portion where the protrusive members 32, 34 are disposed, as it is spread out 360° in the circumferential direction thereof. In FIG. 3A, for an easier understanding of the illustration, a second wire E1b which provides the one energizing path E1 is indicated by the solid lines, and a second wire E2b which provides the other energizing path E2 is indicated by the broken lines. This also holds true for FIG. 3B.

As shown in FIGS. 2 and 3A, the protrusive members 32, 34 are in the form of thin rectangular plates which are arrayed on an outer surface of the balloon 20 along the circumferential direction thereof and which project radially-outwardly from the balloon 20. The protrusive members 32, 34 are provided as a plurality of (three in the present embodiment) pairs of protrusive members 32, 34 juxtaposed in the circumferential direction of the balloon 20 (see also FIGS. 5A and 5B). The protrusive members 32, 34 are fused or bonded to the surface of the balloon 20, for example.

The protrusive members 32, 34 may be arrayed in appropriate patterns. For example, the protrusive members 32, 34 in each pair may be closely positioned with a spacing of 30°, therebetween, and the pairs of protrusive members 32, 34, i.e., one predetermined pair of protrusive members 32, 34 and another pair of protrusive members 32, 34, may be spaced from each other by an interval of 90°. Alternatively, all the protrusive members 32, 34 may be spaced at equal intervals of 60°, for example.

Figure 5A:
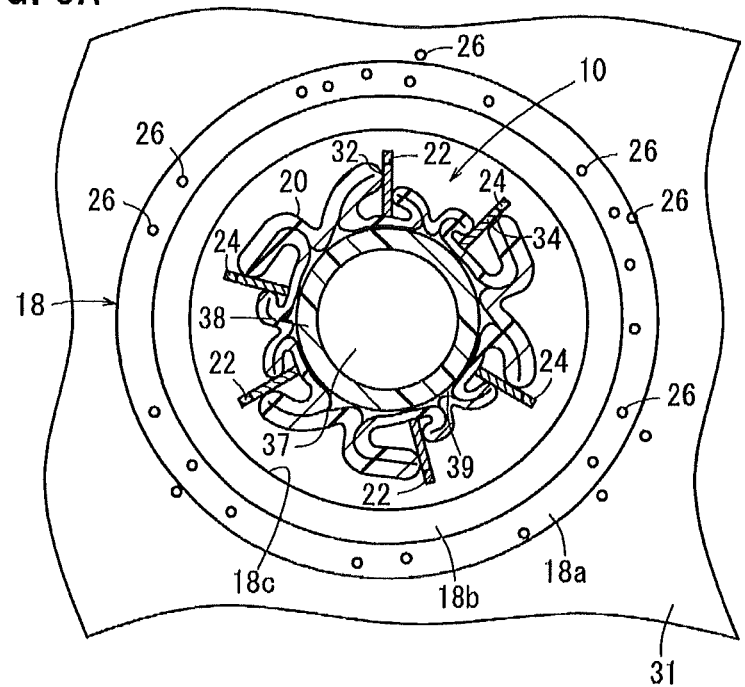
FIG. 5A is a cross-sectional view of the balloon which is inserted into a renal artery.
Figure 5B:
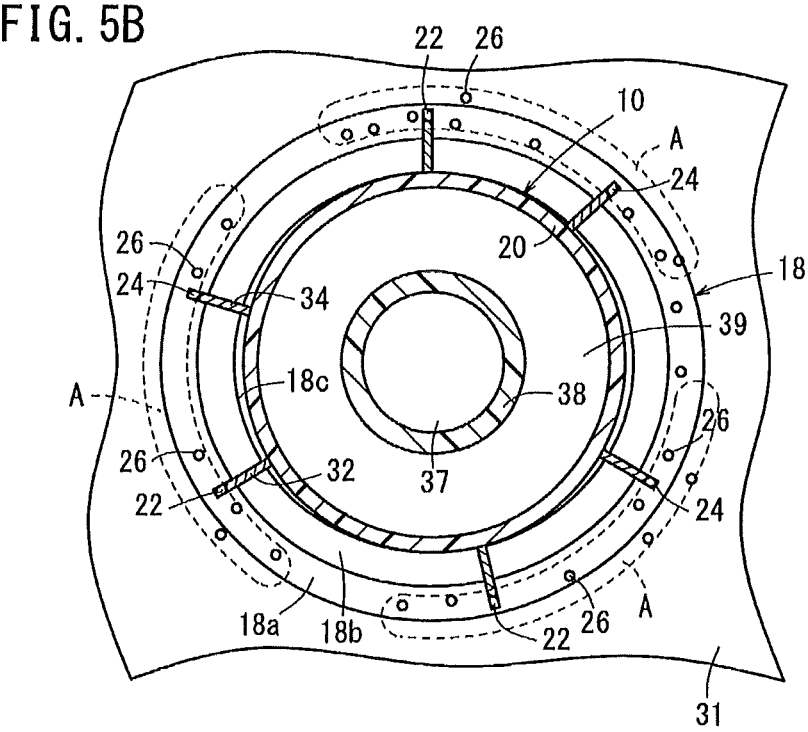
FIG. 5B is a cross-sectional view of the balloon which is inflated from the state shown in FIG. 5A.

As shown in FIG. 5B, when the balloon 20 is inflated, the protrusive members 32, 34 function as cutting edges (blades, cutting members) which cut into the renal artery 18 from an intima 18c to a media 18b thereof to deliver the electrodes 22, 24 on their tip ends into a region near an adventitia 18a of the renal artery 18. In other words, the protrusive members 32, 34 should project radially-outwardly from the outer surface of the balloon 20 at least when the balloon 20 is inflated.

The protrusive members 32 (34) including the electrodes 22 (24), i.e., electrode assemblies (cutting edge electrodes, pushing electrodes) of the protrusive members 32 (34) and the electrodes 22 (24), should preferably be of a shape having a width W (see FIG. 2) in the range from about 0.1 mm to 0.15 mm, a height H in the range from about 0.25 mm to 0.35 mm, and an axial length L in the range from about 3 mm to 200 mm so that the electrode assemblies can smoothly cut into the blood vessel wall and the electrodes 22 (24) on the tip end portions of the protrusive members 32 (34) can be positioned appropriately with respect to the sympathetic nerve 26 in the vicinity of the adventitia 18a. The electrodes 22 (24) may have a height which is in the range from about 5% to 50% of the height H. The electrode assemblies may be of any of various shapes other than parallel thin plate shapes, e.g., a triangular cross-sectional shape, a triangular pyramidal shape, a quadrangular pyramidal shape, or the like. When the balloon 20 with the protrusive members 32, 34 mounted thereon is inflated, its tubular portion may have an outside diameter in the range from about 3 mm to 6 mm and a length in the range from about 8 mm to 30 mm.

The protrusive members 32, 34 are made of an insulative material such as resin, e.g., acryl, nylon, PET, PP, ABS, or the like, or ceramics or the like, or are made of metal with its surface coated with an insulating film (e.g., an insulating coating such as a resin coating of parylene, PTFE, or the like). Therefore, the protrusive members 32, 34 serve as electrically insulative members. When a living body between the electrodes 22, 24 is energized with high-frequency energy, a current is prevented from being applied between the protrusive members 32, 34, but is caused to be applied selectively between only the electrodes 22, 24 on the tip ends of the protrusive members 32, 34 in each pair.

The protrusive members 32, 34 may be made of a material whose electric resistance is sufficiently greater than the electrodes 22, 24, rather than an insulative material, so that the protrusive members 32, 34 can function as electrically insulative members as a current is essentially applied only between the electrodes 22, 24.

The electrodes 22, 24 are mounted in pairs on adjacent ones of the protrusive members 32, 34. According to the present embodiment, three pairs of the electrodes 22, 24 are mounted on adjacent ones of the protrusive members 32, 34, and the energizing paths E1, E2 are connected to the electrodes 22, 24 (see FIGS. 2 and 3A). The electrodes 22, 24 in the pairs function as active electrodes and return electrodes, providing bipolar electrodes for bipolar energization of living bodies. Though the electrodes 22, 24 are provided as three pairs of bipolar electrodes in the present embodiment, they may be provided as one or two pairs or four or more pairs of bipolar electrodes.

The electrodes 22, 24 are disposed on the respective projecting tip end portions (tip end faces) of the protrusive members 32, 34. The electrodes 22, 24 may be in the form of thin metal plates or the like joined to the tip end portions of the protrusive members 32, 34 or predetermined electrical conductors applied by brazing and solidified on the tip end portions of the protrusive members 32, 34. However, the electrodes 22, 24 may be of any constitution insofar as it is capable of supplying a predetermined high-frequency current to living bodies.

Next, the energizing paths E1, E2 that are connected from the high-frequency power supply 30 to the electrodes 22, 24 comprise first wires E1a, E2a connected by connectors to the high-frequency power supply 30 and extending up to a position near the opening 36 in the shaft 14, and second wires E1b, E2b connected to the distal ends of the energizing cables E1a, E2a and extending from the position near the opening 36 to the electrodes 22, 24.

The first wires E1a, E2a may comprise bendable electric wires in the form of electrically conducive wires covered with insulation (insulated-covered electric wires), and have suitable specifications in view of voltages applied to living bodies and compatibility with living bodies. As shown in FIGS. 1 and 4B, the first wires E1a, E2a extend from the opening 36 in the shaft 14 to the proximal end side thereof, and are disposed on an outer surface of the outer tube 40 of the shaft 14 with the inflating lumen formed therein. The first wires E1a, E2a and the outer tube 40 are covered with a covering member 41 such as a heat-shrinkable tube or the like. The first wires E1a, E2a have their proximal ends spaced from the shaft 14 and connected by connectors to the high-frequency power supply 30.

Figure 4A:
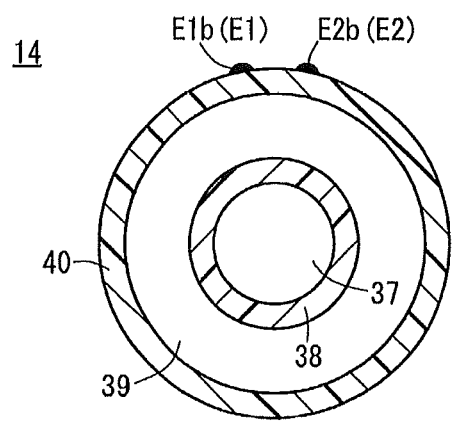
FIG. 4A is a cross-sectional view taken along line IVA-IVA of FIG. 1.
Figure 4B:
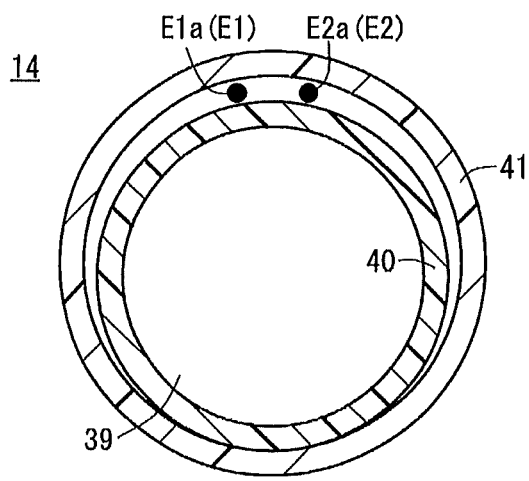
FIG. 4B is a cross-sectional view taken along line IVB-IVB of FIG. 1.

As shown in FIGS. 2 and 4A, the second wires E1b, E2b may preferably be in the form of printed wires that extend from the ends of the electrodes 22, 24 over side faces (front and rear end faces) of the protrusive members 32, 34 and are disposed on the outer surface of the balloon 20 and the outer surface of the shaft 14. The second wires E1b, E2b may have suitable specifications in view of voltages applied to living bodies and compatibility with living bodies.

In the energizing paths E1, E2, the first wires E1a, E2a and the second wires E1b, E2b are disposed respectively on proximal and distal end sides of the opening 36, and are joined to each other in the vicinity of the opening 36, e.g., at a position immediately prior to the opening 36.

The distal end side of the shaft 14, which will be positioned on the distal side in the body cavity, has its outside diameter minimized by the second wires E1b, E2b in the form of printed wires. The proximal end side of the shaft 14 is of simple low-cost constitution due to the first wires E1a, E2a in the form of electric wires. As connectors can easily be connected to the proximal ends of the first wires E1a, E2a, the first wires E1a, E2a can easily be connected to the high-frequency power supply 30. The portion of the shaft 14 on the proximal end side of the opening 36 may comprise a base tube, not shown, having a certain large tube rigidity which is coupled to the outer tube 40. Even with such constitution, the first wires E1a, E2a can easily be fixed to the circumferential surface of the base tube by the covering member 41. Accordingly, the shaft 14 can be manufactured with increased efficiency. Of course, the first wires E1a, E2a may comprise printed wires as with the second wires E1b, E2b, and the second wires E1b, E2b may comprise electric wires as with the first wires E1a, E2a.

As shown in FIG. 2, for example, radiopaque markers M may be disposed on the circumferential surface of the inner tube 38 which extends through the balloon 20 in order to allow the user to visually recognize the positions of the balloon 20 and the electrodes 22, 24 when the balloon catheter 10 is used in radioscopy. The radiopaque markers M that are positioned in alignment with the distal and proximal ends of the electrodes 22 (24) or in alignment with the distal and proximal ends of the cylindrical portion of the balloon 20, for example, make it possible to visually recognize more accurately the axial positions of the balloon 20 and the electrodes 22 (24). Of course, the radiopaque markers M may be disposed at the distal and proximal ends of the protrusive members 32 (34) or at the distal and proximal ends of the electrodes 22 (24). The radiopaque markers M are made of a material (radiopaque material) opaque to X rays (radiations) such as gold, platinum, tungsten, or the like, so that they are visible under radioscopy even when they are placed in living bodies.

A process of treating the sympathetic nerve 26 using the energizing system 12 which incorporates the balloon catheter 10 constituted as described above according to the present embodiment will be described by way of example below.

The balloon catheter 10 and the energizing system 12 which incorporates the balloon catheter 10 are used on patients with intractable hypertension who find it difficult to improve their high blood pressure even by taking antihypertensive, for example. The balloon catheter 10 and the energizing system 12 are used in a treatment for lowering the blood pressure by cauterizing the sympathetic nerve 26 around the renal artery 18 to block its neurotransmission function.

In substantially the same manner as with a medical procedure for indwelling a general balloon catheter in a renal artery, the guide wire 35 and a guiding catheter 33 (see FIG. 1) are inserted from a femoral artery toward the renal artery 18 with the sympathetic nerve 26 therearound to be cauterized until the guide wire 35 and the guiding catheter 33 reach the renal artery 18 while they are being imaged under radioscopy.

Then, as shown in FIG. 5A, the balloon catheter 10 with the balloon 20 folded is inserted into the body through the lumen of the guiding catheter 33 while being guided by the guide wire 35, and caused to ascend under radioscopy until the balloon 20 with the electrodes 22, 24 on the tip ends of the protrusive members 32, 34 reaches a position in the vicinity of the center of the renal artery 18. While the balloon 20 is being folded, the protrusive members 32, 34 and the electrodes 22, 24 are stored by being surrounded by the folded balloon 20. Therefore, the balloon catheter 10 can pass smoothly through the guiding catheter 33 and the blood vessel. FIG. 5A shows the folded balloon 20 by way of example. The balloon 20 may be folded in other configurations, e.g., the balloon 20 may be folded with the protrusive members 32 lying down.

Then, the balloon 20 is inflated in the renal artery 18 to cause the protrusive members 32, 34 to cut into the blood vessel wall until the electrodes 22, 24 reach a region near the adventitia 18a for cauterizing the sympathetic nerve 26.

An inflating fluid is delivered under pressure into the inflating lumen 39 formed in and extending through the shaft 14, inflating the balloon 20. As shown in FIG. 5B, the protrusive members 32, 34 projecting from the outer surface of the balloon 20 puncture the intima 18c and the media 18b of the renal artery 18 until the electrodes 22, 24 on the tip ends reach a region within or in the vicinity of the adventitia 18a. In FIGS. 5A and 5B, the reference character 31 represents an extravascular tissue (surrounding tissue) such as fat or the like which is present around the renal artery 18.

The user then turns on a predetermined power supply switch, to energize the high-frequency power supply 30 to supply a high-frequency current through the energizing paths E1, E2 (the first wires E1a, E2a and the second wires E1b, E2b) to be applied between the electrodes 22, 24 in the pairs. Regions that are disposed between the electrodes 22, 24 in the pairs, which serve as bipolar electrodes, and regions in their periphery (e.g., cauterized regions A surrounded by the broken lines in FIG. 5B) are cauterized, damaging the sympathetic nerve 26 together with part of the adventitia 18a thereby to block the neurotransmission function thereof. Thereafter, the balloon 20 is shrunk to pull the protrusive members 32, 34 out of the blood vessel wall. The balloon catheter 10 is then removed out of the body, and the incision made in the thigh for inserting the balloon catheter 10 is closed. The treating process is now ended.

With the balloon catheter 10 according to the present embodiment, as described above, the protrusive members 32, 34 which project outwardly at least when the balloon 20 is inflated are mounted on the outer surface of the balloon 20, and the electrodes 22, 24 for transmitting energy, e.g., a high-frequency current, to a living body tissue are mounted on the respective projecting tip end portions of the protrusive members 32, 34. When the balloon 20 is inflated in the renal artery 18, for example, the protrusive members 32, 34 cut into the wall of the renal artery 18 to cause the electrodes 22, 24 on the tip ends to pass through the intima 18c and the media 18b of the renal artery 18 until they reach the adventitia 18a with ease. As indicated by the cauterized regions A shown in FIG. 5B, the adventitia 18a and the sympathetic nerve 26 in its surrounding can selectively be cauterized while any adverse effects on the intima 18c and the media 18b of the renal artery 18 are being minimized, so that the neurotransmission function of the sympathetic nerve 26 can be blocked for treating hypertension.

Since the protrusive members 32, 34 are erected on the outer surface of the balloon 20 and the electrodes 22, 24 are mounted on the tip end portions of the protrusive members 32, 34, the electrodes 22, 24 can be delivered easily and accurately to a desired depth in the body cavity and can selectively supply a high-frequency current only in their neighborhood. Specifically, the height H (see FIG. 2) of the protrusive members 32, 34 may be set to an appropriate value depending on an object to be treated, such as the sympathetic nerve 26, so that only such an object to be treated which may be located deeply in the blood vessel wall can be selectively cauterized while preventing the blood vessel wall from being cauterized in its entirety. Furthermore, as energy is transmitted to only the object to be treated and its vicinity, the efficiency with which to cauterize the object to be treated is high.

The balloon catheter 10 has at least a pair of protrusive members 32, 34, and the electrodes 22, 24 mounted respectively on the protrusive members 32, 34 serve as a pair of bipolar electrodes. The electrodes 22, 24 can locally energize a living body tissue to be energized, e.g., the sympathetic nerve 26, while reliably preventing other living body tissues, e.g., the intima 18c of the renal artery 18, from being energized.

As the protrusive members 32, 34, which serve as a basis for the electrodes 22, 24, are arrayed along the circumferential directions of the balloon 20, the electrodes 22, 24 can be placed in an appropriate position in the renal artery 18 without the need for any special process of positioning the electrodes 22, 24 in the renal artery 18 for determining a cauterizing position, and the electrodes 22, 24 thus placed can appropriately and reliably disrupt the sympathetic nerve 26 which is disposed along and around the renal artery 18. Stated otherwise, with the layout of the protrusive members 32, 34 (the electrodes 22, 24) on the surface of the balloon 20 being appropriately set in advance depending on an object to be treated, the electrodes 22, 24 do not need to be positioned in a blood vessel under radioscopy, and hence the medical treatment process involving the balloon catheter 10 is simple and highly accurate.

Inasmuch as the protrusive members 32, 34, which serve as a basis for the electrodes 22, 24 for transmitting energy to a living body tissue, are insulative, the region that is energized by the electrodes 22, 24 is limited to a desired region. The intima 18c and the media 18b of the blood vessel are thus prevented from being energized between the protrusive members 32, 34.

Normally, the blood vessel wall such as of the renal artery 18 or the like is so soft that the protrusive members 32, 34 in the form of thin plates to some extent can sufficiently function as cutting edges and cut into the blood vessel wall even if the protrusive members 32, 34 are not sharp in shape. However, depending on the nature of the blood vessel wall, the protrusive members 32, 34 may not cut into the blood vessel wall sufficiently, and depending on the state and type of the blood vessel wall, it may not be preferable for the protrusive members 32, 34 to cut into the blood vessel wall.

Figure 6:
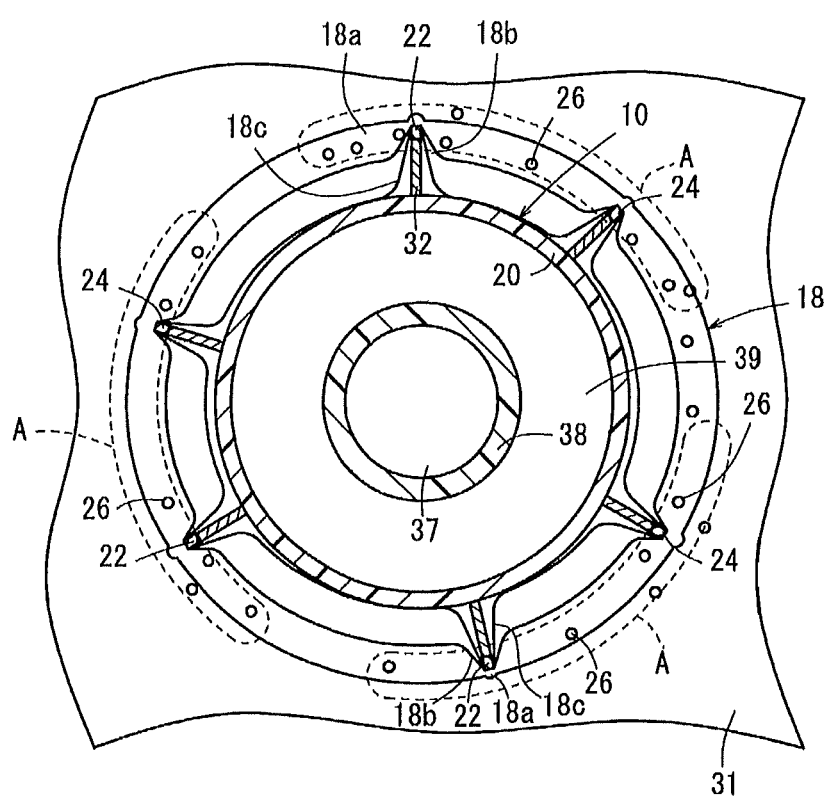
FIG. 6 is a cross-sectional view of the balloon with protrusive members pushing the intima of the renal artery toward the adventitia thereof.

In this case, as shown in FIG. 6, the protrusive members 32, 34 do not cut into the blood vessel wall, but press the blood vessel wall from within the blood vessel and push the intima 18c and the media 18b into the blood vessel wall to deliver the electrodes 22, 24 on the tip ends to the vicinity of the adventitia 18a and the sympathetic nerve 26 therearound. The cauterized ranges A then include part of the intima 18c and the media 18b that are pushed and curved by the protrusive members 32, 34. However, since the part of the intima 18c and the media 18b which included in the cauterized ranges A is only a slight proportion of the intima 18c and the media 18b in their entirety, any adverse effects on the entire blood vessel wall are limitative.

Accordingly, the protrusive members 32, 34 may be arranged as cutting edges (cutting edge electrodes) having the electrodes 22, 24 on their leading ends for cutting into the blood vessel wall to deliver the electrodes 22, 24 to a desired depth in the blood vessel wall, or as pushing members (pushing electrodes) having the electrodes 22, 24 on their leading ends for pushing part of the inner surface of the blood vessel wall toward an outer surface of the blood vessel wall to deliver the electrodes 22, 24 to a desired depth in the blood vessel wall when the electrodes 22, 24 are pressed against the blood vessel wall. The protrusive members 32, 34 may be of any constitution insofar as it can deliver the electrodes 22, 24 on the tip ends thereof to a position in the vicinity of an object to be treated.

Figure 3B:
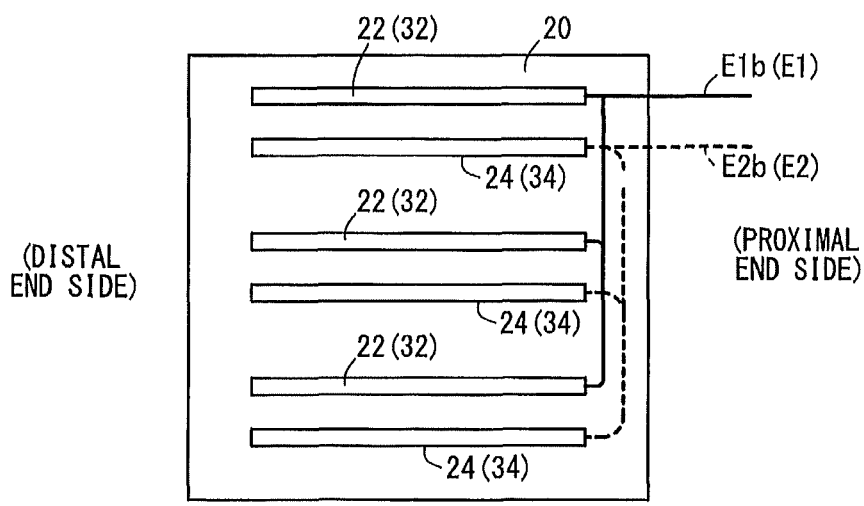
FIG. 3B is a view showing the cylindrical portion of the balloon as it is spread out 360° in the circumferential direction thereof, with a modified wiring structure for electrodes.

The interconnection by energizing paths E1, E2 from the high-frequency power supply 30 to the electrodes 22, 24 may be of constitution other than illustrated above. For example, the first wires E1a, E2a may be inserted through a wire lumen (not shown) juxtaposed in addition to the inflating lumen 39, or may be inserted through the inflating lumen 39, rather than being disposed on the outer circumferential surface of the shaft 14 by the covering member 41 (see FIG. 4B). The second wires E1b, E2b that are wired between the electrodes 22, 24 may be connected parallel to the electrodes 22 and also parallel to the electrodes 24, as shown in FIG. 3B, rather than being connected in series between the electrodes 22 and also in series between the electrodes 24.

The protrusive members for delivering the electrodes 22, 24 to a position in the vicinity of an object to be treated may be of constitution and layouts other than those shown in FIG. 2. Modified constitution and layouts of the protrusive members will be described below.

Figure 7A:
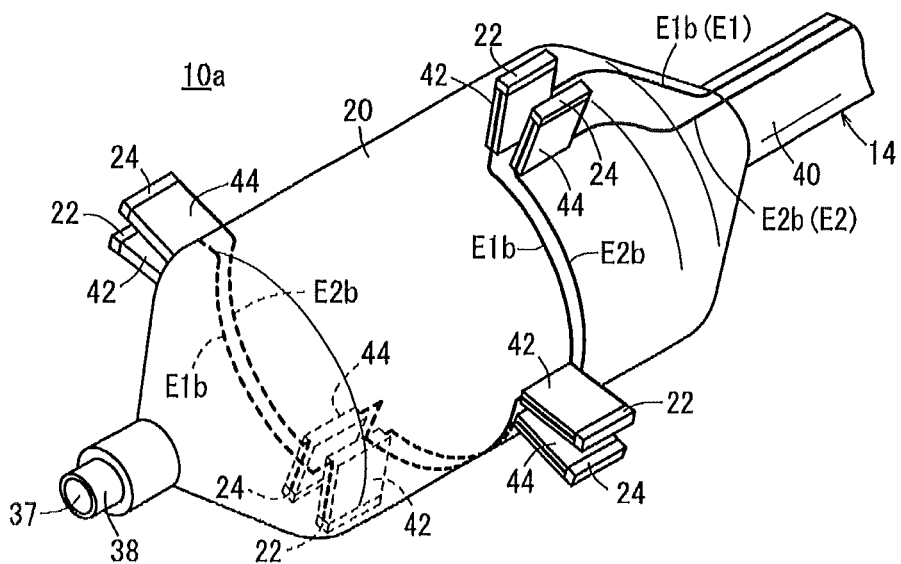
FIG. 7A is an enlarged perspective view of a distal end side of a balloon catheter according to a first modification.
Figure 7B:
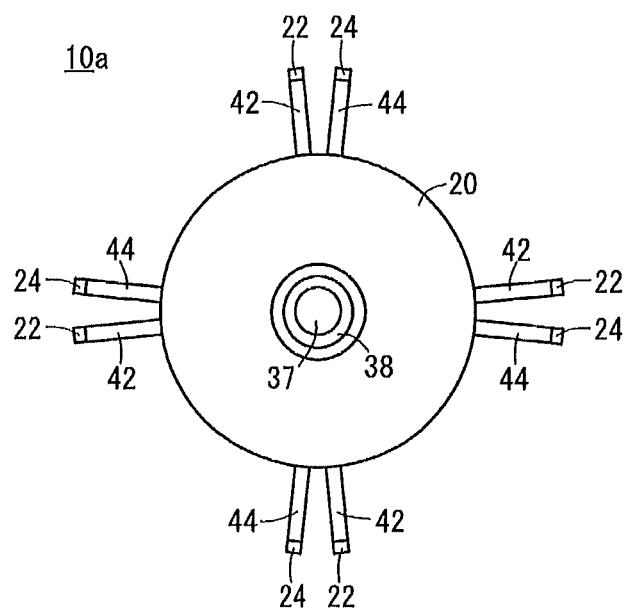
FIG. 7B is a front view of the balloon catheter shown in FIG. 7A.

FIG. 7A is an enlarged perspective view of a distal end side of a balloon catheter 10a according to a first modification, and FIG. 7B is a front view of the balloon catheter 10a shown in FIG. 7A. In FIGS. 7A and 7B, those reference characters which are identical to those shown in FIGS. 1 to 3B denote identical or similar parts, and those parts will not be described in detail below as having identical or similar functions and advantages. This also holds true for other modifications to be described later.

As shown in FIGS. 7A and 7B, the balloon catheter 10a includes a balloon 20 having a plurality of pairs of protrusive members 42, 44 in the form of short, rectangular thin plates disposed on the outer surface of the balloon 20. In each pair, the protrusive members 42, 44 are adjacent to each other in the circumferential directions of the balloon 20. The protrusive members 42, 44 in pairs or sets are provided in a plurality of (four in the first modification) circumferential arrays along an axial direction from the distal end side to the proximal end side of the balloon 20, and are disposed at different circumferential phases. The protrusive members 42, 44 have respective electrodes 22, 24 on their respective tip end portions. The protrusive members 42, 44 may be of the same structural details as the protrusive members 32, 34 except that the protrusive members 42, 44 are of a shape different from the protrusive members 32, 34.

The balloon catheter 10a thus has four circumferential arrays of sets or pairs of protrusive members 42, 44 (the electrodes 22, 24). In each pair or set, the protrusive members 42, 44 are adjacent to each other in the circumferential directions and provide a bipolar electrode. The sets or pairs of protrusive members 42, 44 are arranged from the distal end side to the proximal end side, and are arrayed at different circumferential phases which are equally angularly spaced (by 90° in this embodiment), in the respective arrays. The sets of the electrodes 22, 24 in the arrays are capable of cauterizing the blood vessel wall fully circumferentially at axially spaced positions in a substantially helical pattern.

As a result, the protrusive members 42, 44 (the electrodes 22, 24) are prevented from being concentrating circumferentially at a certain position along the axial direction in which the renal artery 18 extends, and hence are prevented from cauterizing the blood vessel wall in an annular pattern at one location. In other words, the electrodes 22, 24 cauterizes the blood vessel wall at axially distributed positions, but prevents the blood vessel wall from being injured intensively at one location along the axial direction in which the blood vessel extends. Therefore, the sympathetic nerve 26 is reliably cauterized by the electrodes 22, 24 that are disposed in axially distributed arrays, while at the same time any injury caused to the cauterized blood vessel is distributed to prevent the blood vessel from being greatly injured locally.

Since the electrodes 22, 24 are mounted on the protrusive members 42, 44 which are disposed at the different phases in the plural arrays, the electrodes 22, 24 are positioned structurally accurately in the blood vessel. The electrodes 22, 24 thus positioned make it unnecessary to perform a medical procedure for cauterizing a desired region while axially moving and rotating the balloon 20, for example, and hence allow the balloon catheter to be operated simply.

The protrusive members 42, 44 may be of an arrangement other than providing one set of bipolar electrodes in each of the axially distributed arrays as described above. For example, the protrusive members 42, 44 may be arranged to provide two sets of bipolar electrodes in each of the axially distributed arrays. In such a case, the protrusive members 42, 44 in at least axially adjacent arrays should desirably be disposed in different phases.

Figure 8:
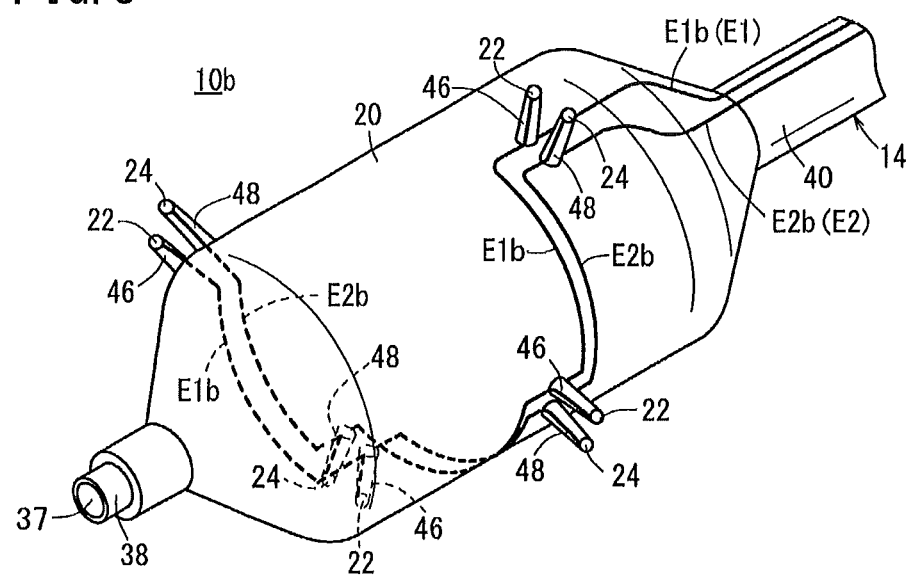
FIG. 8 is an enlarged perspective view of a distal end side of a balloon catheter according to a second modification.

FIG. 8 is an enlarged perspective view of a distal end side of a balloon catheter 10b according to a second modification.

As shown in FIG. 8, the balloon catheter 10b has protrusive members 46, 48 in the form of thin needles, instead of the protrusive members 42, 44 of the balloon catheter 10a shown in FIGS. 7A and 7B, with electrodes 22, 24 mounted on the tip ends of the protrusive members 46, 48. The protrusive members 46, 48 may be of the same structural details as the protrusive members 32, 34 except that the protrusive members 46, 48 are of a shape different from the protrusive members 42, 44.

When the balloon catheter 10b is applied to the renal artery 18, for example, the needle-shaped protrusive members 46, 48 are effective to reduce ranges in which the intima 18c and the media 18b are severed, thereby cauterizing the sympathetic nerve 26 while reducing adverse effects on the entire blood vessel wall. Since the protrusive members 46, 48 are in the form of needles, they can easily cut into soft blood vessel walls or the like and deliver the electrodes 22, 24 smoothly to a desired region to be cauterized.

Essentially as with the balloon catheter 10a, the balloon catheter 10b also prevents the blood vessel wall from being injured intensively at one location along the direction in which the blood vessel extends, and allows the electrodes 22, 24 to be positioned easily in the blood vessel. The needle-shaped protrusive members 46, 48 may be arranged along the circumferential directions, essentially as with the balloon catheter 10a. In such a case, the needle shape of the protrusive members 46, 48 minimizes injury that is caused to the blood vessel wall when it is cut into.

Figure 9:
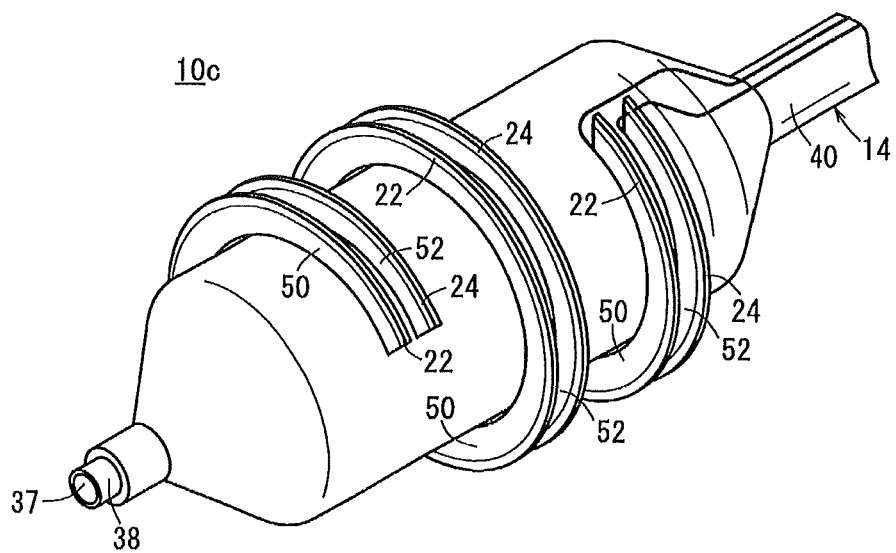
FIG. 9 is an enlarged perspective view of a distal end side of a balloon catheter according to a third modification.

FIG. 9 is an enlarged perspective view of a distal end side of a balloon catheter 10c according to a third modification.

As shown in FIG. 9, the balloon catheter 10c includes a balloon 20 having a pair of helical protrusive members 50, 52 in the form of thin rectangular plates mounted on the outer surface of the balloon 20 and extending helically along an axial direction from the distal end side to the proximal end side of the balloon 20. The protrusive members 50, 52 have respective electrodes 22, 24 on their respective tip end portions. The protrusive members 50, 52 may be of the same structural details as the protrusive members 32, 34 except that the protrusive members 50, 52 are of a shape different from the protrusive members 32, 34.

The helical protrusive members 50, 52 and the electrodes 22, 24 make it possible to cauterize the blood vessel wall along the full circumferential directions thereof at axially different positions, essentially as with the balloon catheters 10a, 10b described above. Consequently, the sympathetic nerve 26 extending along the blood vessel wall can reliably be cauterized by the helical electrodes 22, 24 turned along the axial direction, although the blood vessel wall is prevented from being cauterized intensively at one location along the axial direction. As the second wires E1b, E2b may be joined to the electrodes 22, 24 at respective single spots, the balloon catheter 10c is simplified in structure. Bipolar electrodes provided by the protrusive members 50, 52 (the electrodes 22, 24) may be provided in two or more sets.

The present invention is not limited to the above embodiments, but various arrangements and processes may be employed without departing from the scope of the invention.

What is claimed is:

1. A method for treating a living body tissue by cauterizing a sympathetic nerve around a renal artery to block a neurotransmission function of the sympathetic nerve, comprising the steps of:
   inserting a balloon catheter including a balloon on a distal end side of a shaft into a body cavity, and delivering the balloon to the renal artery;
   inflating the balloon that has been delivered to the renal artery;
   puncturing a blood vessel wall with at least one protrusive member disposed on an outer surface of the balloon when the balloon is inflated; and
   after puncturing the blood vessel wall with the protrusive member, cauterizing the sympathetic nerve within a region at a periphery of an electrode disposed on a projecting tip end portion of the protrusive member by supplying a current to the electrode.

2. The method according to claim 1, wherein, in the puncturing step, the protrusive member extends through an intima and a media of the renal artery so that the electrode reaches a region within or in a vicinity of an adventitia of the renal artery.

3. The method according to claim 1, wherein the current supplied to the electrode in the cauterizing step is a high-frequency current from a high-frequency power supply through an energizing path of the balloon catheter.

4. The method according to claim 3, wherein the energizing path includes printed wiring extending from the electrode over a side face of the protrusive member and arranged on an outer surface of the balloon and an outer surface of the shaft, and the high-frequency current is supplied to the electrode through the print wiring.

5. The method according to claim 1, wherein, in the inserting step, the balloon is inserted into the body cavity in a folded state, with the protrusive member and the electrode being stored inside the folded balloon.

6. The method according to claim 1, wherein, in the puncturing step, the protrusive member extends outwardly from the outer surface of the inflated balloon.

7. The method according to claim 1, wherein the protrusive member and the electrode form an electrode assembly having a width of 0.1 mm to 0.15 mm, a height of 0.25 mm to 0.35 mm and an axial length of 3 mm to 200 mm, and the electrode has a height of about 5% to 50% of the height of the electrode assembly, and the balloon includes a tubular portion having an outer diameter of 3 mm to 6 mm and a length of 8 mm to 30 mm on a condition that the balloon is inflated in the inflating step.

8. The method according to claim 1, wherein the at least one protrusive member includes a plurality of protrusive members, and in the puncturing step, the blood vessel wall is punctured with the protrusive members provided in a plurality of arrays disposed along an axial direction of the balloon and at different circumferential phases of the balloon in the arrays.

9. The method according to claim 1, wherein, in the puncturing step, the blood vessel wall is punctured with the electrode, wherein the protrusive member, which is insulative, makes the electrode positioned away from an outer surface of the balloon.

* * * * *